(12) United States Patent
Li et al.

(10) Patent No.: US 10,653,702 B2
(45) Date of Patent: May 19, 2020

(54) USE OF METAL-ORGANIC FRAMEWORK AS TUMOR ANGIOGENESIS INHIBITOR

(71) Applicant: Yunnan University, Kunming, Yunnan (CN)

(72) Inventors: Bin Li, Yunnan (CN); Daomei Chen, Yunnan (CN); Jiaqiang Wang, Yunnan (CN); Minfang Nie, Yunnan (CN)

(73) Assignee: Yunnan University, Kunming, Yunnan (CN)

( * ) Notice: Subject to any disclaimer, the term of this patent is extended or adjusted under 35 U.S.C. 154(b) by 85 days.

(21) Appl. No.: 15/589,162

(22) Filed: May 8, 2017

(65) Prior Publication Data

US 2017/0319595 A1  Nov. 9, 2017

(30) Foreign Application Priority Data

May 9, 2016 (CN) .......................... 2016 1 0299834

(51) Int. Cl.
*A61K 31/295* (2006.01)
*A61K 31/19* (2006.01)
*A61K 31/555* (2006.01)

(52) U.S. Cl.
CPC ................................ *A61K 31/555* (2013.01)

(58) Field of Classification Search
None
See application file for complete search history.

(56) References Cited

U.S. PATENT DOCUMENTS

2015/0150981 A1* 6/2015 Gref ...................... A61K 47/24
514/777

OTHER PUBLICATIONS

Taylor-Pashow et al., J.Am.Chem.Soc. 2009, 131, 14261-14263, PTO-892.*

* cited by examiner

*Primary Examiner* — Shobha Kantamneni
(74) *Attorney, Agent, or Firm* — MacMillan, Sobanski & Todd, LLC

(57) ABSTRACT

The invention relates to the field of metal-organic framework materials and the field of medical technology, relates to a method for inhibiting tumor angiogenesis or preventing and/or treating tumor, comprising administering to a subject in need thereof an effective amount of a metal-organic framework comprising Fe and ligand. The invention further relates to a method for inhibiting the expression of matrix metalloproteinase in a cell, comprising administering to the cell an effective amount of a metal-organic framework comprising Fe and ligand.

12 Claims, 7 Drawing Sheets

FITC-Annexin V

FITC-Annexin V

USE OF METAL-ORGANIC FRAMEWORK AS TUMOR ANGIOGENESIS INHIBITOR

RELATED APPLICATIONS

This application claims priority to Chinese Application No. 201610299834.6, filed on May 9, 2016, the disclosure of which is incorporated herein by reference in its entirety for all purposes.

TECHNICAL FIELD

The invention relates to the field of metal-organic framework materials and the field of medical technology, relates to a method for inhibiting tumor angiogenesis or preventing and/or treating tumor, and further relates to a method for inhibiting the expression of matrix metalloproteinase in a cell.

BACKGROUND ART

For a long time, tumor is one of the major causes of death in the world. Although there have been relatively mature therapies, many types of tumors lack early symptoms and are not sensitive to radiotherapy and chemotherapy. Many chemotherapeutic agents can damage the immune system in organisms, have toxic and side effects in patients, and result in drug resistance. Especially, when tumor develops to a middle and advanced stage, the speed of treating tumor is generally much slower than the speed of tumor metastasis and spread. Therefore, anti-tumor treatment has always been faced with severe challenges. In order to achieve a better therapeutic effect of tumor, there is a strong demand for novel effective anti-tumor agents and combination therapy strategy.

Antiangiogenesis is regarded as one of the strategies having significant medical value for the treatment of malignant tumor. When tumor volume exceeds 2 $mm^3$, the tumor is in the vascular stage, and the formation of new blood vessels provides the necessary nutritional supply and metabolic excretion for the growth of tumor, resulting in exponential increase in tumor volume. At the same time, since new blood vessels has enhanced permeability, tumor cells can penetrate the blood vessels and migrate to other parts. Therefore, angiogenesis is closely associated with tumor growth, metastasis and recurrence. Blocking tumor angiogenesis and breaking the nutritional supply of tumor tissue have become a new target for anti-tumor therapy, and have also become a hotspot in researches on anti-tumor therapy. The emergence of angiogenesis inhibitors provides a new way for anti-tumor therapy. However, with the enlargement of clinical application and the extension of application time, angiogenesis inhibitors gradually exhibit some side effects. Bevacizumab (Avastin), the first approved drug for inhibiting tumor angiogenesis in the United States, can bind to vascular endothelial growth factor (VEGF) and blocks its biological activity, and is widely applied in clinical treatment now. However, its effect is not satisfactory as it has a lot of serious side effects. Studies show that cancer metastasis is resulted from the co-modulation of multiple growth factors. Therefore, the problem may be solved by the development of novel angiogenesis inhibitors capable of inhibiting multiple growth factors simultaneously.

Matrix metalloproteinases (MMP), a family of zinc-dependent endogenous proteases, have been shown to play an important role in tumour invasion and metastasis and angiogenesis due to their ability to hydrolysis the extracellular matrix. Tumour metastasis is also accompanied by the hydrolysis of extracellular matrix with protease. Therefore, downregulating MMP expression or decreasing MMP protease activity in cell microenvironment is crucial for inhibiting angiogenesis, and preventing tumour invasion and metastasis. Inhibitors targeting to MMP-2 and MMP-9 have been widely applied in tumour-metastasis animal model and been studied in human cancer in clinic. For example, $Fe_3O_4$ nanoparticles coated with piroctone olamine (PO), i.e., $Fe_3O_4$@PO NPs, have the activity of inhibiting MMP-2. The fullerene-based nanoparticle $Gd@C_{82}(OH)_{22}$ and hollow mesoporous carbon nanocapsules (HMCNs), as potent anti-angiogenesis inhibitors, can down-regulate the activity of multiple angiogenic factors including MMP-2 and MMP-9.

Iron is a crucial microelement in organisms. Iron-based complex are effective cytotoxic drugs. Iron-based active compounds are different from the currently used platinum-based drugs in terms of mechanism of action, biological distribution and cytotoxicity, and are effective, or at least substantially effective against cancer that is poorly sensitive to chemotherapy or is resistant to traditional platinum-based drugs. However, there is still no report on the use of iron-based complex as an anti-tumor drug targeting to angiogenesis.

Metal-organic frameworks (MOFs) are a class of porous crystalline materials with periodic multidimensional network structure, formed by self-assembly of metal ions and organic ligands. In recent years, since MOFs have tunable pores and extremely high surface areas, they can be widely applied in multiple fields such as biomedicine, such as encapsulation, delivery, transport and release of drugs, and MOFs can even be used to achieve the gene therapy of disease. Studies have shown that silencing VEGF expression via RNA interference can inhibit tumor angiogenesis and block tumor growth. Therefore, Fe-containing metal-organic frameworks can be used to prepare novel anti-tumor angiogenesis inhibitors, in order to achieve the effect of anti-tumor therapy. Now, there is no report on the inhibition of MMPs or anti-angiogenesis by MOFs materials themselves.

SUMMARY OF INVENTION

In the invention, unless otherwise specified, the scientific and technical terms used herein have the meanings as generally understood by a person skilled in the art. Moreover, the laboratory operating steps as involved herein are the conventional steps widely used in the corresponding fields. Moreover, in order to understand the invention better, definitions and explanations are provided for the following terms.

In the invention, the term "metal-organic framework" refers to a crystal compound having a periodic network structure, formed by self-assembly of oxygen-containing polydentate organic ligands and metal ions.

In the invention, Fe-containing metal-organic frameworks (Fe-MOFs) refer to crystal compounds having three-dimensional network structures, consisting of Fe ions linking to organic ligands (such as 1,3,5-benzenetricarboxylic acid, terephthalic acid, and fumaric acid). Fe-MOFs include, but are not limited to Fe-MIL-101, Fe-MIL-100, Fe-MIL-88A and Fe-MIL-88B, and the ligands comprised therein, the crystal forms and the molecular formula are shown in the following table:

| Fe-MOFs | Ligand | Crystal form | Molecular formula |
|---|---|---|---|
| Fe-MIL-101 | terephthalic acid | octahedron | $Fe_3O(H_2O)_2F[C_6H_4(CO_2)_2)]_3$ |
| Fe-MIL-100 | 1,3,5-benzenetricarboxylic acid | octahedron | $Fe_3O(H_2O)_2F[C_6H_3(CO_2)_3)]_2$ |
| Fe-MIL-88A | Fumaric acid | hexangular rod | $Fe_3O(O_2CC_2H_2CO_2)_3(H_2O)_2(NO_3)]n$ |
| Fe-MIL-88B | terephthalic acid | hexangular rod | $Fe_3O(CH_3OH)_3[C_6H_3(CO_2)_2]_3 \cdot CH_3CO_2 \cdot (CH_3OH)_{4.5}$ |

With respect to the papers on Fe-MOFs, please see, for example:

Fe-MIL-100: Chen W, Zhang Z, Bao W, et al. Hierarchical mesoporous $\gamma$-$Fe_2O_3$/carbon nanocomposites derived from metal organic frameworks as a cathode electrocatalyst for rechargeable Li—$O_2$ batteries [J]. Electrochimica Acta, 2014, 134: 293-301.

Fe-MIL-88A: Lee H J, Cho W, Lim E, et al. One-pot synthesis of magnetic particle-embedded porous carbon composites from metalorganic frameworks and their sorption properties. Chemical Communications, 2014, 50(41): 5476-5479.

Fe-MIL-88B: Laurier K G M, Vermoortele F, Ameloot R, et al. Iron (III)-based metalorganic frameworks as visible light photocatalysts. Journal of the American Chemical Society, 2013, 135(39): 14488-14491.

Common methods for preparing Fe-MOFs include, but are not limited to hydrothermal synthesis and microwave-assisted synthesis. In some embodiments of the present application, Fe-MOFs are prepared by hydrothermal synthesis, comprising: at a high temperature (e.g., 100-1000° C. and a high pressure (e.g., 1 MPa-1 GPa), reacting organic ligands (such as 1,3,5-benzenetricarboxylic acid, terephthalic acid, and fumaric acid) with Fe-containing metal compounds in an aqueous solution. In hydrothermal synthesis, a Teflon-lined autoclave is generally used as a reaction vessel, and the reaction is carried out in an oven.

In the invention, the term "Fe-MIL-101" refers to a metal-organic framework (with a molecular formula of $Fe_3O(H_2O)_2F[C_6H_4(CO_2)_2)]_3$, and a structural formula as follows, and its exemplified XRD diffraction pattern is shown in FIG. 1) having a three-dimensional network octahedral structure, formed by linking $Fe^{3+}$ to terephthalic acid. With respect to the papers on Fe-MIL-101, please see, for example, Taylor-Pashow K M L, Della Rocca J, Xie Z, et al. Post-synthetic modifications of iron-carboxylate nanoscale metal-organic frameworks for imaging and drug delivery. Journal of the American Chemical Society, 131(40): 14261-14263 (2009).

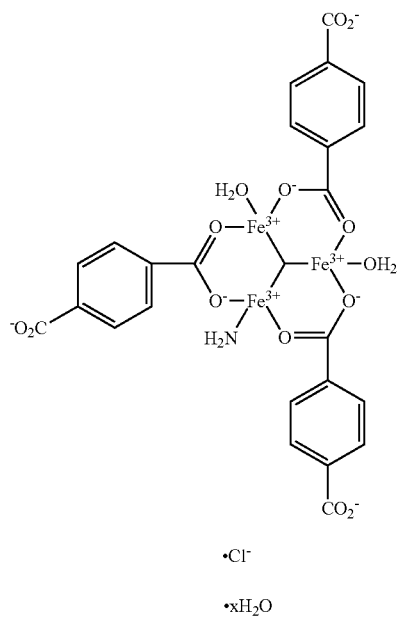

Methods for preparing Fe-MIL-101 can be found in, for example, Skobelev, I. Y, Sorokin, A. B., Kovalenko, K. A., Fedin, V. P. & Kholdeeva, O. A. Solvent-free allylic oxidation of alkenes with $O_2$ mediated by Fe- and Cr-MIL-101. J. Catal. 298, 61-69 (2013), and Taylor-Pashow K M L, Della Rocca J, Xie Z, et al. Post-synthetic modifications of iron-carboxylate nanoscale metal-organic frameworks for imaging and drug delivery [J]. Journal of the American Chemical Society, 131(40): 14261-14263 (2009).

As used herein, the term "aromatic polycarboxylic acid" includes, but is not limited to aromatic bicarboxylic acid and aromatic tricarboxylic acids, e.g., benzene-containing bicarboxylic acids (e.g., phthalic acid, terephthalic acid, isophthalic acid), or benzene-containing tricarboxylic acids (e.g., 1,3,5-benzenetricarboxylic acid, 1,2,4-benzenetricarboxylic acid).

As used herein, the term "aliphatic polycarboxylic acid" includes, but is not limited to aliphatic bicarboxylic acids and aliphatic tricarboxylic acids, saturated polycarboxylic acids and unsaturated polycarboxylic acid, e.g., oxalic acid, malonic acid, succinic acid, glutaric acid, adipic acid, maleic acid, fumaric acid.

As used herein, the term "an effective amount" refers to an amount that is sufficient to achieve or at least partially achieve a desired effect. For example, a prophylactically effective amount refers to an amount that is sufficient to prevent, suppress or delay the development of a disease; a therapeutically effective amount refers to an amount that is sufficient to cure or at least partially suppress a disease and its complications in a patient with the disease. It is completely within the ability of a person skilled in the art to determine such an effective amount. For example, the "effective amount" not only depends on the type and severity of a disease or condition in a subject, but also depends on the general conditions of a subject such as age, body weight and gender, administration route of a drug, other therapy used in combination, and the like.

By deep research and creative work, the inventors found that Fe-containing metal-organic frameworks can inhibit the expression of matrix metalloproteinase (e.g., MMP-2 and MMP-9), and can inhibit tumor angiogenesis. On the basis of this, the following invention is provided.

In an aspect, the present application provides a method for inhibiting tumor angiogenesis or preventing and/or treating tumor, comprising administering to a subject in need thereof an effective amount of a metal-organic framework comprising Fe and ligand.

In some embodiments, the metal-organic framework comprises Fe(III).

In some embodiments, the ligand is selected from a group consisting of aromatic polycarboxylic acid and aliphatic polycarboxylic acid, such as 1,3,5-benzenetricarboxylic acid, terephthalic acid, and fumaric acid.

In some embodiments, the metal-organic framework compound comprises $Fe^{3+}$.

In some embodiments, the metal-organic framework comprises aromatic polycarboxylate anion and/or aliphatic polycarboxylate anion.

In some embodiments, the metal-organic framework compound further comprises halogen ion (e.g., fluorine ion, bromine ion, chlorine ion or iodine ion).

In some embodiments, the metal-organic framework further comprises crystal water.

In some embodiments, the metal-organic framework is selected from a group consisting of Fe-MIL-101, Fe-MIL-100, Fe-MIL-88A and Fe-MIL-88B.

In some embodiments, the metal-organic framework is Fe-MIL-101.

In some embodiments, the metal-organic framework has a Langmuir specific surface area of 4500-5500 $m^2\ g^{-1}$, e.g., 4500 $m^2\ g^{-1}$, 4600 $m^2\ g^{-1}$, 4700 $m^2\ g^{-1}$, 4800 $m^2\ g^{-1}$, 4900 $m^2\ g^{-1}$, 5000 $m^2\ g^{-1}$, 5100 $m^2\ g^{-1}$, 5200 $m^2\ g^{-1}$, 5300 $m^2\ g^{-1}$, 5400 $m^2\ g^{-1}$ or 5500 $m^2\ g^{-1}$.

In some embodiments, the metal-organic framework has a BET specific surface area of 2000-4000 $m^2\ g^{-1}$, e.g., 2000-2500 $m^2\ g^{-1}$, 2500-3000 $m^2\ g^{-1}$, 3000-3500 $m^2\ g^{-1}$ or 3500-4000 $m^2\ g^{-1}$, e.g., 2000 $m^2\ g^{-1}$, 2100 $m^2\ g^{-1}$, 2200 $m^2\ g^{-1}$, 2300 $m^2\ g^{-1}$, 2400 $m^2\ g^{-1}$, 2500 $m^2\ g^{-1}$, 2600 $m^2\ g^{-1}$, 2700 $m^2\ g^{-1}$, 2800 $m^2\ g^{-1}$, 2900 $m^2\ g^{-1}$, 3000 $m^2\ g^{-1}$, 3100 $m^2\ g^{-1}$, 3200 $m^2\ g^{-1}$, 3300 $m^2\ g^{-1}$, 3400 $m^2\ g^{-1}$, 3500 $m^2\ g^{-1}$, 3600 $m^2\ g^{-1}$, 3700 $m^2\ g^{-1}$, 3800 $m^2\ g^{-1}$, 3900 $m^2\ g^{-1}$ or 4000 $m^2\ g^{-1}$.

In some embodiments, said effective amount is 0.1 μg/kg/day-250 mg/kg/day, e.g., 0.1 μg/kg/day-1 μg/kg/day, 1 μg/kg/day-50 μg/kg/day, 50 μg/kg/day-100 μg/kg/day, 100 μg/kg/day-500 μg/kg/day, 500 μg/kg/day-1 mg/kg/day, 1 mg/kg/day-25 mg/kg/day, 25 mg/kg/day-50 mg/kg/day, 50 mg/kg/day-100 mg/kg/day or 100 mg/kg/day-250 mg/kg/day.

In some embodiments, the tumor angiogenesis is angiogenesis of tumor pathogenic tissue or angiogenesis caused by tumor.

In some embodiments, the tumor is selected from a group consisting of esophageal cancer (such as esophageal adenocarcinoma and esophageal squamous cancer), brain tumor, lung cancer (such as small cell lung cancer and non-small cell lung cancer), squamous cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, solid tumor, Non-Hodgkin's Lymphomas, central nervous system tumor (such as neuroglioma, glioblastoma multiforme, glioma or sarcoma), prostatic cancer and thyroid cancer.

In some embodiments, the tumor is selected from a group consisting of non-small cell lung cancer and ovarian cancer.

In some embodiments, the subject is a mammal.

In some embodiments, the subject is selected from a group consisting of bovine, equine, caprid, suidae, canine, feline, rodent, and primate.

In some embodiment, the subject is human.

In some embodiments, the metal-organic framework may be prepared in any pharmaceutically acceptable dosage form for administration to a subject, such as tablets, capsules, pills, granules, solutions, suspensions, syrups, injections (including injection, sterile powder for injection and concentrated solution for injection), suppositories, inhalants, spraying agents or preparations for external application. In addition, the metal-organic framework may be administered to a subject in need of this therapy by any suitable route, such as external application, oral administration, parenteral administration, rectal administration, intrapulmonary administration, or topical administration, etc. When administered orally, the metal-organic framework may be prepared into an oral formulation, such as an oral solid formulation, such as tablet, capsule, pill, and granule; or may be prepared into an oral liquid formulation, such as oral solution, oral suspension, and syrup; the oral formulation may comprise suitable fillers, binders, disintegrants, lubricants and the like. When administered parenterally, the metal-organic framework may be prepared into an injection, including injection, sterile powder for injection and concentrated solution for injection. When administered rectally, the metal-organic framework may be prepared into a suppository, etc. When administered intrapulmonarily, the metal-organic framework may be prepared into inhalant, or spraying agent, etc.

In some embodiments, the metal-organic framework is present in a therapeutically and/or prophylactically effective amount in the formulation. In some embodiments, the metal-organic framework is present in a form of unit dose in the formulation.

In an aspect, the present application provides a method for inhibiting the expression of matrix metalloproteinase in a cell, comprising administering to the cell an effective amount of a metal-organic framework comprising Fe and ligand.

In some embodiments, the metal-organic framework comprises Fe(III).

In some embodiments, the ligand is selected from a group consisting of aromatic polycarboxylic acid and aliphatic polycarboxylic acid, such as 1,3,5-benzenetricarboxylic acid, terephthalic acid, and fumaric acid.

In some embodiments, the metal-organic framework comprises $Fe^{3+}$.

In some embodiments, the metal-organic framework comprises aromatic polycarboxylate anion and/or aliphatic polycarboxylate anion.

In some embodiments, the metal-organic framework further comprises halogen ion (e.g., fluorine ion, bromine ion, chlorine ion or iodine ion).

In some embodiments, the metal-organic framework further comprises crystal water.

In some embodiments, the metal-organic framework is selected from a group consisting of Fe-MIL-101, Fe-MIL-100, Fe-MIL-88A and Fe-MIL-88B.

In some embodiments, the metal-organic framework is Fe-MIL-101.

In some embodiments, the metal-organic framework has a Langmuir specific surface area of 4500-5500 $m^2$ $g^{-1}$, e.g., 4500 $m^2$ $g^{-1}$, 4600 $m^2$ $g^{-1}$, 4700 $m^2$ $g^{-1}$, 4800 $m^2$ $g^{-1}$, 4900 $m^2$ $g^{-1}$, 5000 $m^2$ $g^{-1}$, 5100 $m^2$ $g^{-1}$, 5200 $m^2$ $g^{-1}$, 5300 $m^2$ $g^{-1}$, 5400 $m^2$ $g^{-1}$ or 5500 $m^2$ $g^{-1}$.

In some embodiments, the metal-organic framework has a BET specific surface area of 2000-4000 $m^2$ $g^{-1}$, e.g., 2000-2500 $m^2$ $g^{-1}$, 2500-3000 $m^2$ $g^{-1}$, 3000-3500 $m^2$ $g^{-1}$ or 3500-4000 $m^2$ $g^{-1}$, e.g., 2000 $m^2$ $g^{-1}$, 2100 $m^2$ $g^{-1}$, 2200 $m^2$ $g^{-1}$, 2300 $m^2$ $g^{-1}$, 2400 $m^2$ $g^{-1}$, 2500 $m^2$ $g^{-1}$, 2600 $m^2$ $g^{-1}$, 2700 $m^2$ $g^{-1}$, 2800 $m^2$ $g^{-1}$, 2900 $m^2$ $g^{-1}$, 3000 $m^2$ $g^{-1}$, 3100 $m^2$ $g^{-1}$, 3200 $m^2$ $g^{-1}$, 3300 $m^2$ $g^{-1}$, 3400 $m^2$ $g^{-1}$, 3500 $m^2$ $g^{-1}$, 3600 $m^2$ $g^{-1}$, 3700 $m^2$ $g^{-1}$, 3800 $m^2$ $g^{-1}$, 3900 $m^2$ $g^{-}$; or 4000 $m^2$ $g^{-1}$.

In some embodiments, the method comprises: administering to the cell the metal-organic framework at a final concentration of 3-50 μg $mL^{-1}$ (e.g., 3-20 μg $mL^{-1}$, 20-30 μg $mL^{-1}$, 30-40 μg $mL^{-1}$ or 40-50 μg $mL^{-1}$; e.g., 3 μg $mL^{-1}$, 5 μg $mL^{-1}$, 7 μg $mL^{-1}$, 9 μg $mL^{-1}$, 10 μg $mL^{-1}$, 12.5 μg $mL^{-1}$, 15 μg $mL^{-1}$, 17.5 μg $mL^{-1}$, 20 μg $mL^{-1}$, 22.5 μg $mL^{-1}$, 25 μg $mL^{-1}$, 27.5 μg $mL^{-1}$, 30 μg $mL^{-1}$, 32.5 μg $mL^{-1}$, 35 μg $mL^{-1}$, 37.5 μg $mL^{-1}$, 40 μg $mL^{-1}$, 42.5 μg $mL^{-1}$, 45 μg $mL^{-1}$, 47.5 μg $mL^{-1}$ or 50 μg $mL^{-1}$).

In some embodiments, the matrix metalloproteinase is selected from a group consisting of MMP-2, MMP-9 and a combination thereof.

In some embodiments, the method is performed in vivo or in vitro; preferably, the method is performed in vivo, for example, is applied to a subject (e.g., mammal, such as bovine, equine, caprid, suidae, canine, feline, rodent, and primate; e.g., human), in order to reduce or inhibit the activity of matrix metalloproteinase in the cell of the subject; or the method is performed in vitro, for example, is applied to an in vitro cell (e.g., a cell line or a cell from a subject such as cancer cell), in order to reduce or inhibit the activity of matrix metalloproteinase in the in vitro cells.

In some embodiments, the cell is a tumor cell.

In some embodiments, the cell is selected from esophageal cancer cell (e.g., esophageal adenocarcinoma cell and esophageal squamous cancer cell), brain tumor cell, lung cancer cell (e.g., small cell lung cancer cell and non-small cell lung cancer cell), squamous cell cancer cell, bladder cancer cell, gastric cancer cell, ovarian cancer cell, peritoneal cancer cell, pancreatic cancer cell, breast cancer cell, head and neck cancer cell, cervical cancer cell, endometrial cancer cell, colorectal cancer cell, liver cancer cell, renal cancer cell, solid tumor cell, Non-Hodgkin's Lymphomas cell, central nervous system tumor cell (e.g., neuroglioma cell, glioblastoma multiforme cell, glioma cell or sarcoma cell), prostatic cancer cell and thyroid cancer cell; or, the cell is a primary cell from the subject or culture thereof, or an established cell line.

In some embodiments, the cell is selected from a group consisting of non-small cell lung cancer cell and ovarian cancer cell.

In another aspect, the present application provides use of a metal-organic framework as an anti-tumor angiogenesis inhibitor, characterized in that the metal-organic framework is Fe-MIL-101, which has a Langmuir and BET specific surface area of 5400 $m^2$ $g^{-1}$ and 3710 $m^2$ $g^{-1}$, respectively, and an effective concentration of 12.5-25 μg $mL^{-1}$.

The use of a metal-organic framework as an anti-tumor angiogenesis inhibitor, characterized in that the angiogenesis is angiogenesis of tumor pathogenic tissue and angiogenesis caused by tumor.

The use of a metal-organic framework as an anti-tumor angiogenesis inhibitor, characterized in that the tumor is human non-small cell lung cancer (A549) and human ovarian cancer (SKOV3); the vascular endothelial cell for angiogenesis is human umbilical vein endothelial cell (HUVEC); the normal cell as control is mouse embryonic fibroblast (BABL-3T3).

The use of a metal-organic framework as an anti-tumor angiogenesis inhibitor, characterized in that the angiogenesis inhibitor selectively inhibits the proliferation of cancer cell and vascular endothelial cell, but has a weak toxicity on normal cell.

The use of a metal-organic framework as an anti-tumor angiogenesis inhibitor, characterized in that the angiogenesis inhibitor has the function of inhibiting migration of cancer cell and vascular endothelial cell; and has the function of inhibiting formation of tubule in vitro and down-regulating expression of matrix metalloproteinase (MMP-2 and MMP-9) in cell microenvironment.

The angiogenesis inhibitor can inhibit tube formation of human vein vascular endothelial cells induced by VEGF and human ovarian cancer cell (SKOV3) conditioned medium (CM) in vitro, and its effect is stronger than that of the traditional tyrosine kinase inhibitor (SU5416).

Beneficial Effects of the Invention

In the invention, Fe-containing metal-organic frameworks (e.g., Fe-MIL-101) are used to inhibit the expression of matrix metalloproteinase (e.g., MMP-2 and MMP-9), and selectively inhibit proliferation and migration of tumor cells and human vascular endothelial cells. These results show that Fe-containing metal-organic frameworks can be used to inhibit tumor angiogenesis, and can be used to prevent and/or treat tumor.

The embodiments of the invention are illustrated in detail by combining the following drawings with examples. However, it is understood by those skilled in the art that the following drawings and examples are used only for the purpose of illustrating the invention, rather than limiting the protection scope of the invention. According to the detailed description of the drawings and the preferred embodiments, the purposes and beneficial effects of the invention will be obvious for a person skilled in the art.

DESCRIPTION OF THE DRAWINGS

FIG. 10 is the developing result in Example 7, wherein, FIG. 10A-C show the expression levels of MMP-2 and MMP-9 in SKOV3 cell, VEGF-stimulated HUVEC cell, and CM-stimulated HUVEC cell, respectively.

SPECIFIC MODES FOR CARRYING OUT THE INVENTION

Figure 1:
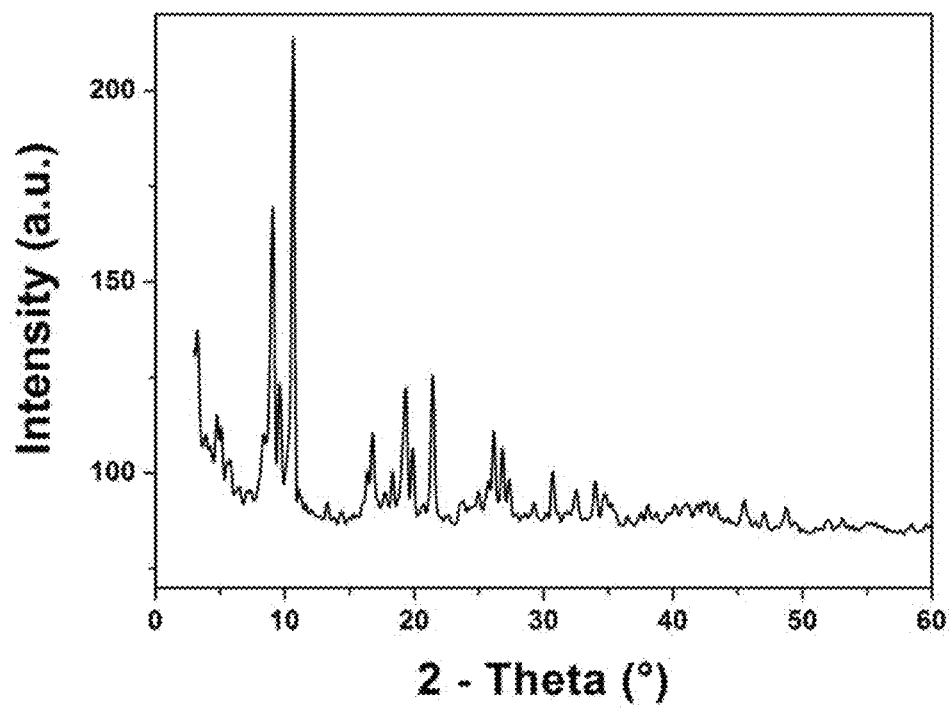
FIG. 1 shows the X-ray diffraction (XRD) pattern of Fe-MIL-101 in Example 1.

The embodiments of the invention are illustrated in detail by reference to the following examples. However, a person skilled in the art will understand that the examples are used only for the purpose of illustrating the invention, rather than limiting the protection scope of the invention. When the conditions are not indicated in the Examples, the Examples are carried out under the conventional conditions or the conditions recommended by the manufacturers. The reagents or instruments used in the present invention, the manufacturers of which are not indicated, are the conventional products that are commercially available.

Chemicals and Instrumentation

Terephthalic acid (H$_2$BDC, 99%), ferric chloride hexahydrate (FeCl$_3$.6H$_2$O, 99%), ethanol (99.5%), and N,Ndimethylformamide (DMF, 99.9%) were purchased from Alfa Aesar (Ward Hill, Mass.) and used for synthesis. All organic solvents were of analytical grade. The Annexin-V/PI detection apoptotic kit and JC1 lipophilic cation (5,5', 6,6'tetrachloro 1,1',3,3' tetraethyl benzimidazolcarbocyanine iodide) were from Beyotime Institute of Biotechnology (Jiangsu, China).

Fourier transform infrared measurements were performed on a Nicolet 8700 instrument. X-ray powder diffraction (XRD) experiments were conducted on a D/max-3B spectrometer with Cu Kα radiation. Pore size distributions, BET surface areas and pore volumes were measured by nitrogen adsorption/desorption measurements using a Micromeritics Tristar II Surface area and porosity analyser. Prior to the analysis, the samples were degassed at 90° C. for 1 h. Inductively coupled plasma-atomic emission spectrometry (ICP-AES) analysis was used to determine the contents of Fe$^{3+}$ released from Fe-MIL-101. ICP-AES measurement was carried out with a Shimadzu ICPS-1000IV model. Cells were analysed using a FACSCalibur flow cytometer (Becton Dickinson & Co., Franklin Lakes, N.J.) and an Olympus IX73 microscope.

Example 1 Synthesis and Characterization of Fe-MIL-101

MOF Fe-MIL-101 was synthesized with ferric hydroxide and terephthalic acid according to the literature (Skobelev, I. Y., Sorokin, A. B., Kovalenko, K. A., Fedin, V. P. & Kholdeeva, O. A. Solvent-free allylic oxidation of alkenes with O$_2$ mediated by Fe- and Cr-MIL-101. J. Catal. 298, 61-69 (2013). Taylor-Pashow K M L, Della Rocca J, Xie Z, et al. Post-synthetic modifications of iron-carboxylate nanoscale metal-organic frameworks for imaging and drug delivery. J. Am. Chem. Soc. 131(40): 14261-14263 (2009)). Briefly, FeCl$_3$.6H$_2$O (0.675 g, 2.45 mmol) and H$_2$BDC (0.206 g, 1.24 mmol) were added slowly into DMF (15 mL) solution. The mixture was stirred for 10 min at room temperature, and then transferred into a Teflon-lined stainless steel autoclave and heated at 110° C. for 20 h. The resulting brown solid was filtered off, and the raw product was purified by washing in hot ethanol (70° C., 3 h), filtered off, and dried in an oven (70° C., 30 min). The particles were isolated by centrifuging and washed with DMF and ethanol to remove any unreacted starting materials.

Figure 2:
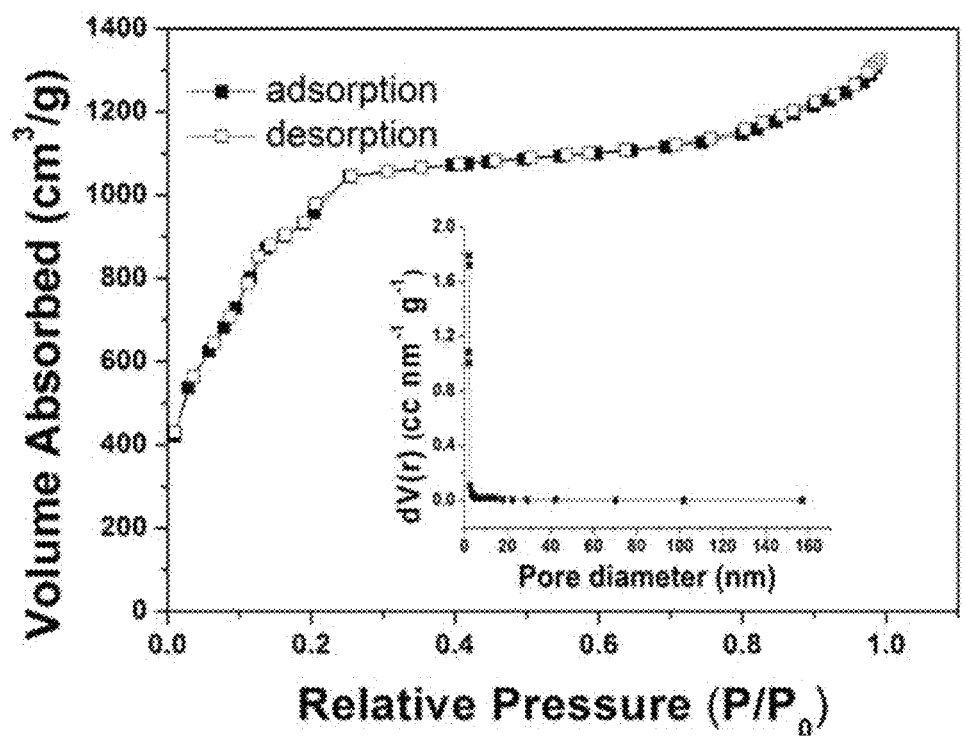
FIG. 2 shows $N_2$ adsorption/desorption isotherm and the BJH pore-size distribution (inset) of Fe-MIL-101 in Example 1.
Figure 3:
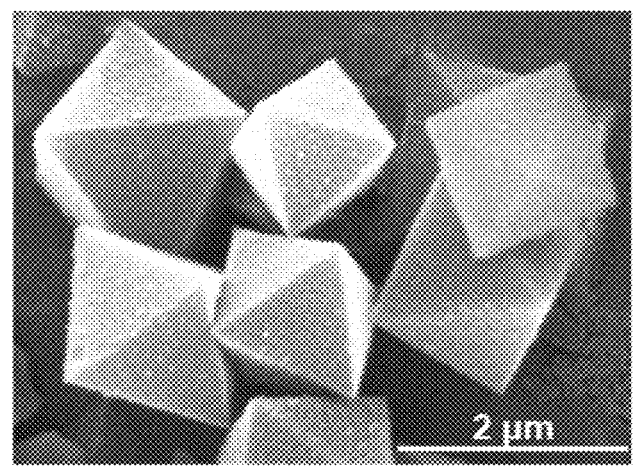
FIG. 3 is the SEM photograph of Fe-MIL-101 in Example 1.

The X-ray diffraction (XRD) pattern of Fe-MIL-101 was shown in FIG. 1. The diffraction peaks all corresponded to the product synthesized by Skobelev (Skobelev, I. Y., Sorokin, A. B., Kovalenko, K. A., Fedin, V. P. & Kholdeeva, O. A. Solvent-free allylic oxidation of alkenes with O$_2$ mediated by Fe- and Cr-MIL-101. J. Catal. 298, 61-69 (2013)). N$_2$ adsorption/desorption isotherm and the BJH pore-size distribution (inset) of Fe-MIL-101 were shown in FIG. 2. The adsorption/desorption isotherm of Fe-MIL-101 is of type I, indicating the presence of the microporous network. the Langmuir surface area of Fe-MIL-101 prepared by the method of this example is 5400 m$^2$ g$^{-1}$, and the Brunauer-Emmer-Teller (BET) surface area is 3710 m$^2$ g$^{-1}$. The SEM photograph of Fe-MIL-101 was shown in FIG. 3. Together these results confirmed the proper synthesis of Fe-MIL-101.

Example 2 Effect of Fe-MIL-101 on Cell Growth

The cytotoxicity of Fe-MIL-101 in three cell lines (A549, SKOV3 and HUVEC cells) and normal mouse embryonic fibroblast BABL-3T3 cells was evaluated by the MTT assay.

Cell culture: BABL-3T3 (mouse embryonic fibroblasts cells), A549 (human lung adenocarcinoma cells), and SKOV3 (human ovarian cancer cells) were purchased from the American Type Culture Collection (ATCC, Manassas, Va., USA). The BABL-3T3 cell line was cultured in DMEM (high glucose) and other cells were grown in DMEM (low glucose) containing 10% fetal bovine serum. HUVECs were isolated from term umbilical cord veins using collagenase and cultured in DMEM supplemented with 20% fetal bovine serum. All cell lines were grown at 37° C. in a humidified 5% CO$_2$ atmosphere. HUVEC cells were used within 6 passages.

MTT assay: A549 cell, SKOV3 cell, HUVEC cell and BABL-3T3 cell in logarithmic growth phase, were seeded in 96-well plates at a density of 1×10$^4$ cells per well. When the cells were at a confluence of 80%, Fe-MIL-101 at a concentration of 1.56, 3.125, 6.25, 12.5, and 25 μg mL$^{-1}$ was added, respectively. Three parallel wells were used for each concentration. After reaction for 72 h, 5 μg mL$^{-1}$ MTT was added to each well, and the cells were further cultured for 4 h. The supernatant was drawn, and 150 μL DMSO was added to each well. After horizontal vibration for 10 min, absorbance (OD value) at a wavelength of 490 nm was determined using a microplate reader. The experiment was repeated for three times.

The cell inhibition rate is calculated in accordance with the following formula: cell inhibition rate %=[1−([OD]$_{test}$/[OD]$_{control}$)]×100%, wherein [OD]$_{test}$ refers to the OD value for the test group, and [OD]$_{control}$ refers to the OD value for the control group. IC$_{50}$ value refers to the concentration of a drug at which the inhibition rate of cells reaches 50%.

Figure 4:
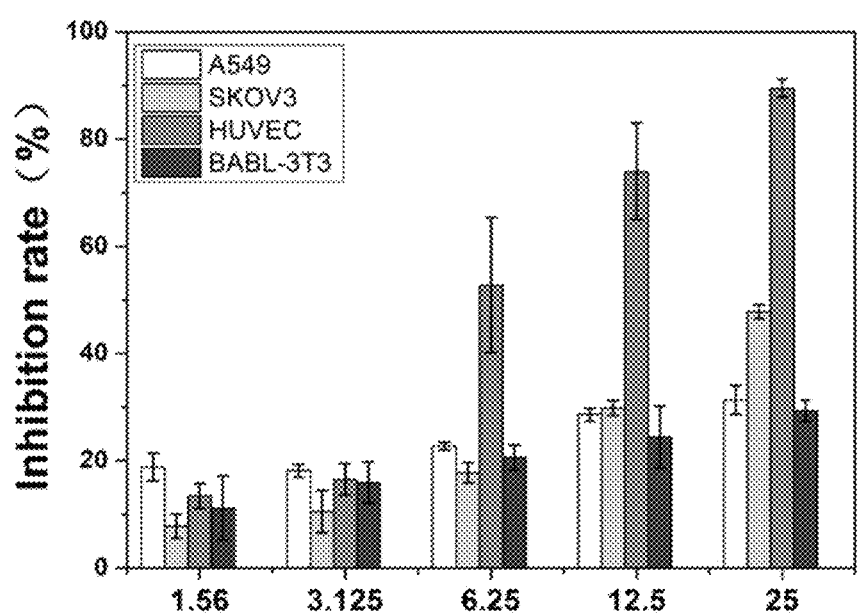
FIG. 4 shows the inhibition rate of Fe-MIL-101 on A549, SKOV3, HUVEC and BABL-3T3 cell in Example 2.

Results and discussion: FIG. 4 shows the inhibition rate of Fe-MIL-101 on A549, SKOV3, HUVEC and BABL-3T3 cell. As shown in FIG. 4, Fe-MIL-101 has the function of inhibiting the proliferation of tumor cell and vascular endothelial cell in a dose-dependent manner. In particular, it is most effective in inhibiting SKOV3 and HUVEC cell. When Fe-MIL-101 is at a concentration of 12.5 μg mL$^{-1}$, its inhibition rate is greater than 30% for the tumor cell (A549 and SKOV3), and is close to 80% for HUVEC; when Fe-MIL-101 is at a concentration of 25 μg mL$^{-1}$, its inhibition rate is greater than 50% and 90% for SKOV3 and HUVEC cell, respectively. It can be determined by calculation that the IC$_{50}$ value of Fe-MIL-101 is 54.3, 23.6, 9.9 and 78.3 μg mL$^{-1}$ for A549, SKOV3, HUVEC and BABL-3T3 cell, respectively. The results above show that Fe-MIL-101 has a function of selectively inhibiting tumor cell and vascular endothelial cell, and has a good inhibitory effect at a concentration of 12.5-25 μg mL$^{-1}$.

Example 3 Effect of Fe-MIL-101 on HUVEC Proliferation

VEGF plays various functions in endothelial cells, including the induction of proliferation and differentiation. Conditioned media (CM) from SKOV3 cells can induce an increase in the proliferation of HUVECs. The effect of Fe-MIL-101 on HUVEC proliferation treated with VEGF or CM collected from SKOV3 cells were assessed.

Method

Conditioned media (CM) was collected from P6 SKOV3 cells. Cells at 80-90% confluence were washed with PBS three times and incubated with fresh DMEM without FBS medium (1 mL of medium per 9 cm$^2$ of growth area) for 24 h at 37° C. Media were then centrifuged (600 g, 10 min, 4° C.) and stored at −80° C. for further experiments.

Proliferation was assessed using the MTT assay in 96-well plates. HUVECs were incubated for 24 h in 10% FBS medium, and then replaced with 2% FBS media and incubated overnight before treatment. Vascular endothelial growth factor (VEGF, 10 ng mL$^{-1}$) and antiangiogenic inhibitor SU5416 (20 μM) were used as positive and negative control groups, respectively. Cells were exposed to Fe-MIL-101 (final concentration: 25 μg mL$^{-1}$). In the control group, cells were treated with DMEM. After 24 h, 5 μg mL$^{-1}$ MTT reagent was added in solution for 4 h, and 150 μL DMSO was added into plates for dissolving crystals. Absorbance at 490 nm was determined as described above.

Result

Figure 5:
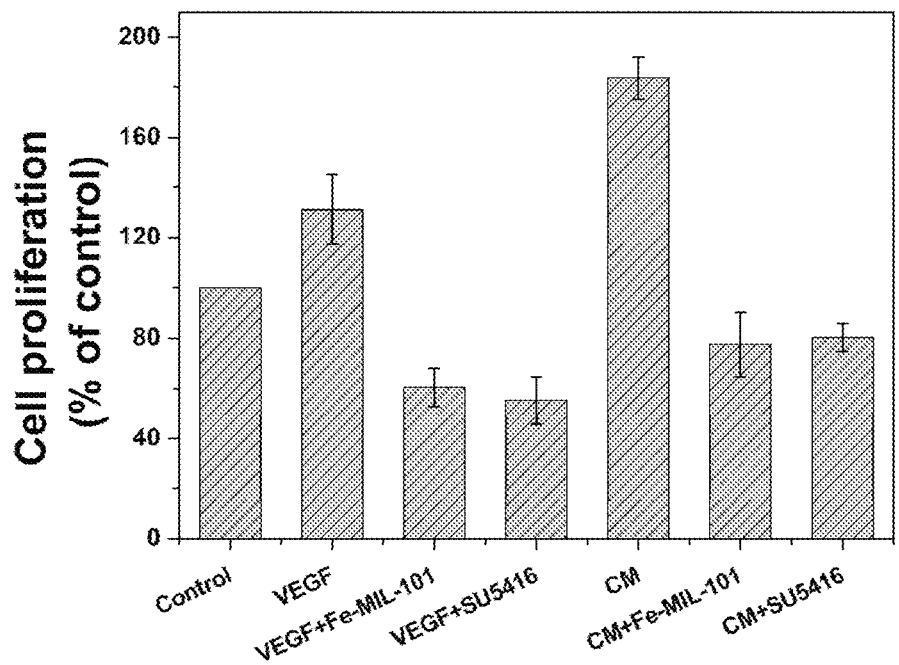
FIG. 5 shows the cell proliferation of HUVECs in Example 3.

The cell proliferation of HUVECs was shown in FIG. 5. As shown in the figure, VEGF increased the proliferation of HUVECs compared with the control group. Moreover, CM from SKOV3 cells induced a significant increase in the proliferation of HUVECs to levels higher than treatment with VEGF. However, Fe-MIL-101 significantly inhibited cell proliferation under VEGF and CM treatment conditions. Furthermore, Fe-MIL-101 displayed a similar or better antiproliferation effect compared with SU5416, a selective inhibitor of VEGF tyrosine kinase activity.

Example 4 Effect of Fe-MIL-101 on the Apoptosis of HUVECs (1) Apoptosis Assay by Hoechst 33342 Staining The nuclear morphology of Fe-MIL-101 treated cells was observed by staining cell nuclei with Hoechst 33342.

Method

HUVEC cells were seeded at a density of 2×10$^5$ cells/well on the surface of a cover slip in a 6-well plate in 2 mL medium containing 10% FBS. After 24 h, cells were treated with Fe-MIL-101 (final concentration: 12.5 or 25 μg mL$^{-1}$) and incubated for 48 h. In the control group, cells were treated with DMEM. Cells were washed with ice-cold PBS, and fixed with 4% paraformaldehyde for 10 min. The cells were incubated with Hoechst 33342 for 15 min at room temperature after washing three times with 2 mL of PBS. The cover slips were mounted on glass slides and the cells were analysed using a confocal fluorescence microscopic system (Olympus IX73, Japan).

Result

Figure 6:
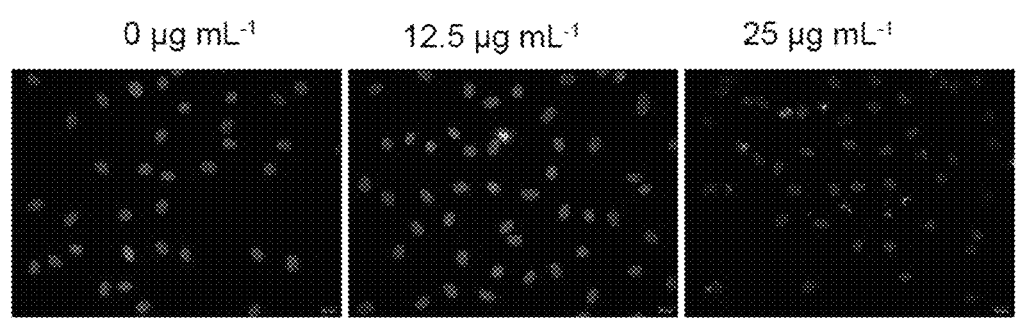
FIG. 6 shows the fluorescence microscopic photographs of control cells and Fe-MIL-101 treated cells in Example 4.
Figure 7A:
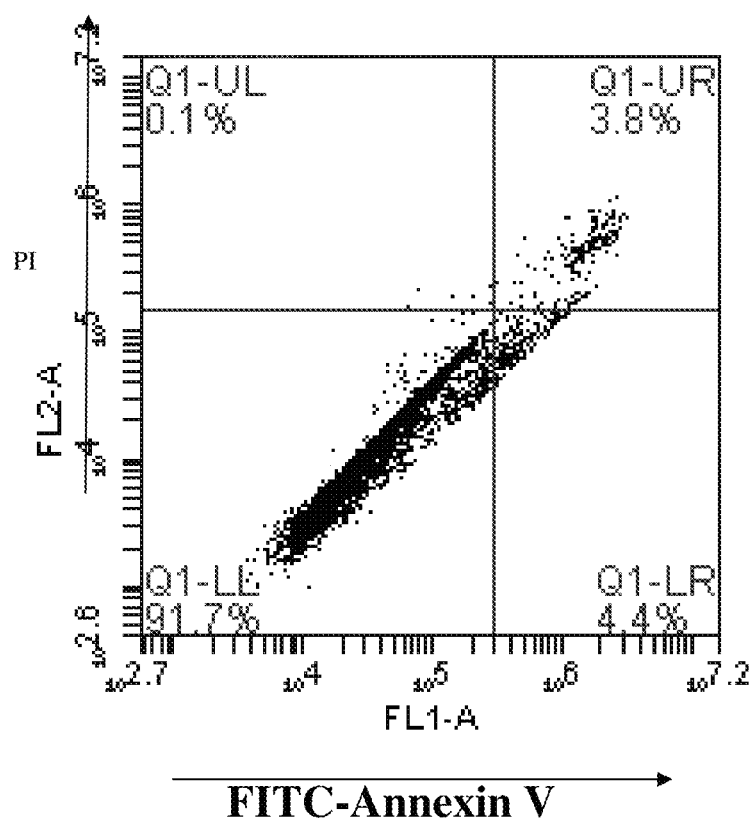
FIG. 7A-7E shows the result of flow cytometer measurement in Example 4, wherein FIGS. 7A-E correspond to the test results of the cells treated with Fe-MIL-101 at a concentration of 0, 3.12, 6.25, 12.5, and 25 μg mL$^{-1}$, respectively.
Figure 7B:
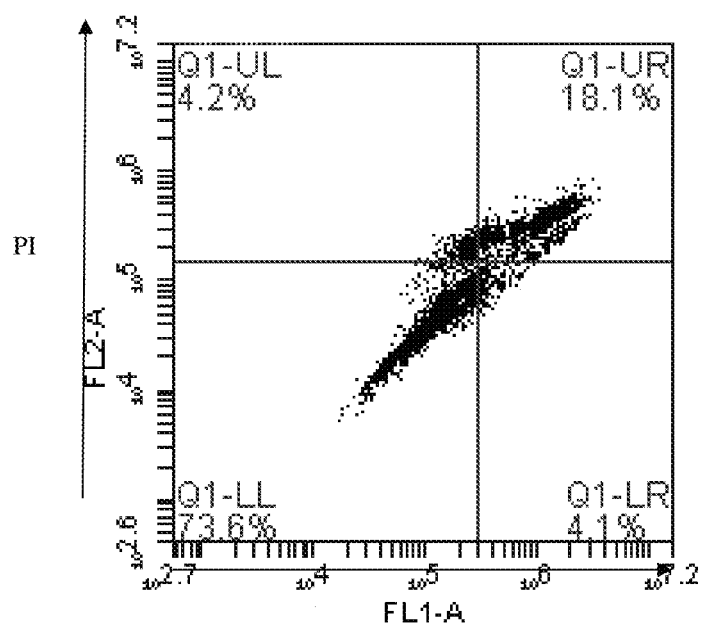
Figure 7C:
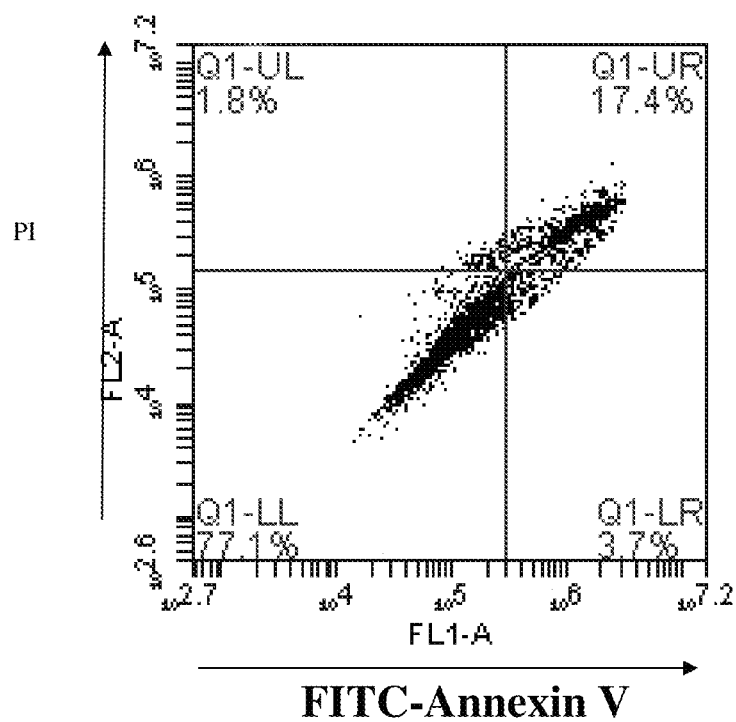
Figure 7D:
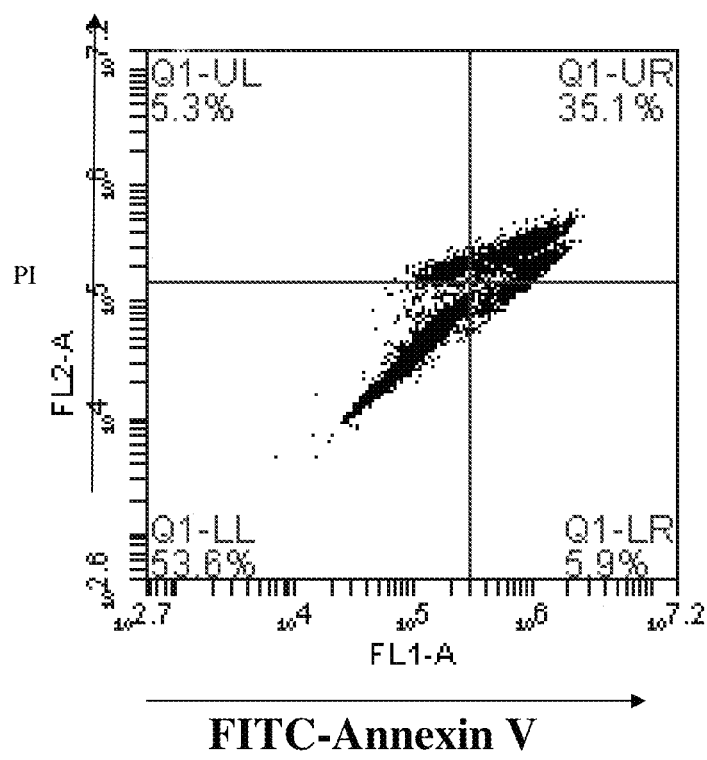
Figure 7E:
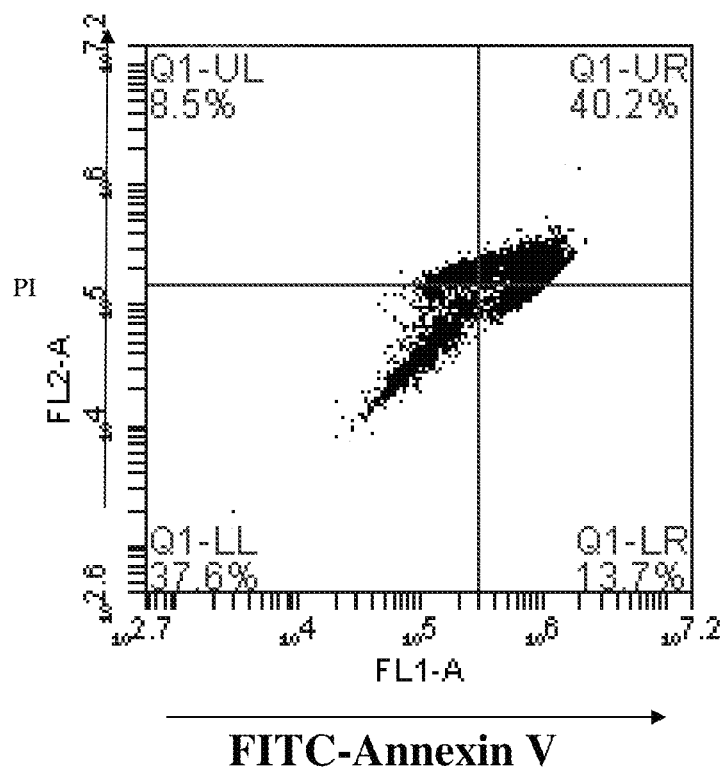

The fluorescence microscopic photographs of control cells (0 μg mL$^{-1}$) and Fe-MIL-101 treated cells (final concentration: 12.5 μg mL$^{-1}$ and 25 μg mL$^{-1}$) were shown in FIG. 6. As shown in the photographs, control cells, which were uniformly blue, were viable, whereas treated cells showed apoptosis, with nuclear shrinkage, chromatin condensation and cytoplasmic blebbing, and showed bright blue dots in the nuclei, representing nuclear fragmentation.

(2) Flow Cytometry Analysis of Apoptotic and Necrotic Cells.

The FITC-Annexin-V and PI binding assay was used to further confirm Fe-MIL-101-induced apoptosis Method Chemical treatment: after cell seeding, Fe-MIL-101 (at a final concentration of: 0, 3.12, 6.25, 12.5, 25 μg mL$^{-1}$) was added to the cells at a confluence of 80%, and the treatment was carried out for 24 h.

After chemical treatment, cells (1×10$^6$) were harvested, washed with PBS, fixed with 70% ethanol, and maintained at 4° C. for at least 12 h. Pellets were stained with the fluorescent probe solution containing 5 μg mL$^{-1}$ PI and 1 μg mL$^{-1}$ FITC-Annexin-V in PBS on ice in dark for 15 min. The fluorescence emission was measured at 490 nm using 488-nm excitation by a FACSCalibur flow cytometer (Beckman Dickinson & Co., Franklin Lakes, N.J.). A minimum of 1×10$^4$ cells was analysed.

Result

The result of flow cytometer measurement is shown in FIG. 7. In the dual parametric dot plots, the lower left quadrant represents the viable cell population (Annexin-V negative and PI negative), the upper right represents apoptotic cells undergoing secondary necrosis at the last stage or dead cells (Annexin-V and PI double positive), and the lower right represents the early stage apoptotic cell population (Annexin-V positive and PI negative). As the concentration of Fe-MIL-101 increased from 3.12-25 μg mL$^{-1}$, the Annexin-V positive/PI negative cells increased from 3.7% to 13.7%, whereas the double positive cells increased from 17.4% to 40.2%. Increasing numbers of apoptotic cells progressed from the early stage to the late stage resulting in either death or secondary necrosis under Fe-MIL-101 at higher concentrations. This data confirms again that Fe-MIL-101 can effectively induce the apoptosis of HUVECs.

Example 5 Ovarian Cancer Cell and Vascular Endothelial Cell Migration Assay after the Treatment with Fe-MIL-101

Method: The effect of Fe-MIL-101 on the migration ability of SKOV3 cell and HUVEC cell was tested by scratch method. SKOV3 and HUVEC cells were seeded to 6-well plates (2×10$^5$ cell/well), respectively, and cultured for 24 h. After scratching with a 200-μL pipette tip, PBS was used for washing for three times to remove the floating cells. In the experimental group, Fe-MIL-101 was added at a final concentration of 25 μg mL$^{-1}$, and in the control group, DMEM was added. After treating SKOV3 cells and HUVEC cells for 0, 6, 12, 24 h, the number of migrated cells into the scratch area was quantified with a microscope.

Figure 8:
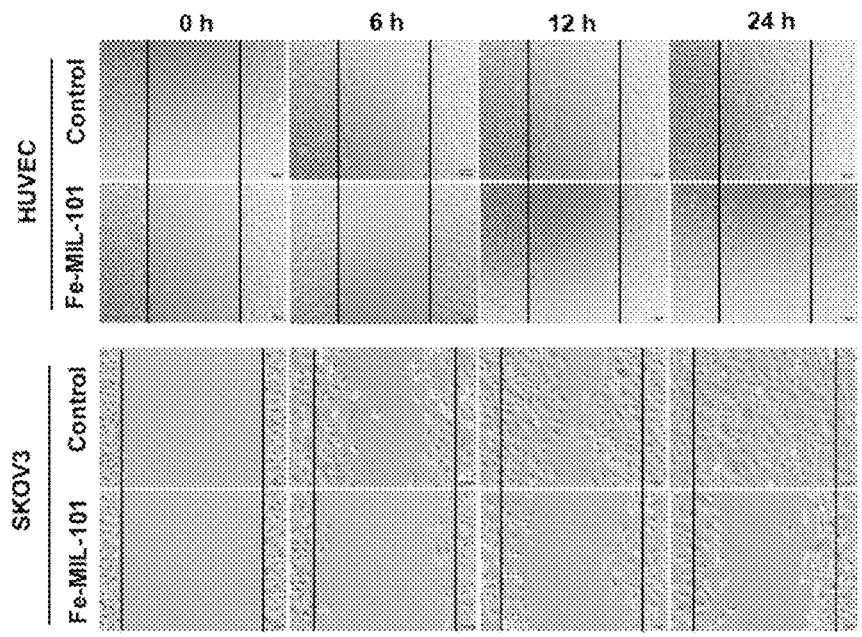
FIG. 8 is the micrographs of the control cell and the cell treated with Fe-MIL-101 at 0, 6, 12, 24 h in Example 5.

Results: FIG. 8 is the micrographs of the control cell and the cell treated with Fe-MIL-101 at 0, 6, 12, 24 h. As shown in FIG. 8, after the treatment with Fe-MIL-101, the number of migrated SKOV3 and HUVEC cells into the scratch area was significantly less than the number of migrated cells into the scratch area in the control group, indicating that Fe-MIL-101 has an inhibitory effect on the migration of the two cells.

Example 6: Experiment on Inhibition of Angiogenesis with Fe-MIL-101

Method: 50 µL Matrigel was added to each well of 96-well plates and the plates were incubated at 37° C. for 30 min for hardening. Then, 100 µL HUVEC suspension ($2\times10^5$ cell/mL) was added gently, and Fe-MIL-101 at 12.5 or 25 µg mL$^{-1}$, VEGF (10 ng mL$^{-1}$) and SKOV3 conditioned media (CM) (0.5 mL), as well as angiogenesis inhibitor SU5416 (20 µM) were added in accordance with the following table, respectively. The cells were cultured for 12 h, and were observed and photographed every 6 hours under a microscope. The experiment was repeated for three times for each group.

| Control group | Experimental group | | | |
|---|---|---|---|---|
| VEGF (10 ng mL$^{-1}$) | VEGF (10 ng mL$^{-1}$) | VEGF (10 ng mL$^{-1}$) | VEGF (10 ng mL$^{-1}$) | |
| | Fe-MIL-101 (12.5 µg mL$^{-1}$) | Fe-MIL-101 (25 µg mL$^{-1}$) | SU5416(20 µM) | |
| CM(0.5 mL) | CM | CM | CM | |
| | Fe-MIL-101 (12.5 µg mL$^{-1}$) | Fe-MIL-101 (25 µg mL$^{-1}$) | SU5416(20 µM) | |

Figure 9:
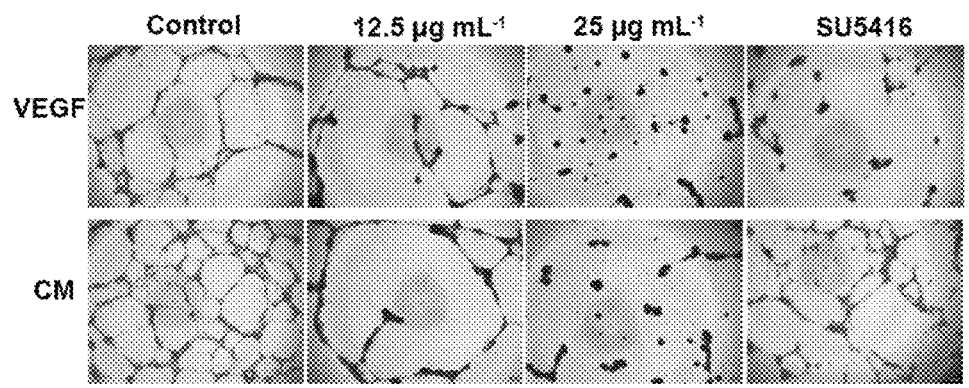
FIG. 9 shows the experimental result on the inhibition of angiogenesis with Fe-MIL-101 in Example 6.

Results: FIG. 9 shows the experimental result on the inhibition of angiogenesis with Fe-MIL-101 12 h later. As shown in FIG. 9, in the control group in which only VEGF or SKOV3 conditioned media (CM) was added, the cells formed good network structures; while in the experimental group in which Fe-MIL-101 was added, the number and length of the tubules decreased rapidly with the increase in the Fe-MIL-101 concentration, and Fe-MIL-101 had a better inhibitory effect than the traditional tyrosine kinase inhibitor SU5416 (20 µM). The experiment shows that Fe-MIL-101 can inhibit VEGF- or tumor CM-stimulated angiogenesis, thereby demonstrating that Fe-MIL-101 is a more potential inhibitor.

Example 7 Experiment on Modulation of the Expression of Matrix Metalloproteinase with Fe-MIL-101 in a Cell Cell treatment: SKOV3 cells were seeded in a 35 mm culture dish. When the cells were at a confluence of 80%, Fe-MIL-101 was added at a final concentration of 12.5 µg mL$^{-1}$ and 25 µg mL$^{-1}$, respectively, and in the control group, the cell culture medium (DMEM) was added. After treating for 24 h, cell proteins were extracted.

HUVEC cells were seeded in a 35 mm culture dish. When the cells were at a confluence of 80%, in the VEGF-stimulated groups, VEGF (20 ng mL$^{-1}$), VEGF (20 ng mL$^{-1}$)+Fe-MIL-101 (12.5 µg mL$^{-1}$), and VEGF (20 ng mL$^{-1}$)+Fe-MIL-101 (25 µg mL$^{-1}$) were added, respectively; in the CM-stimulated groups, CM (20 ng mL$^{-1}$), CM (20 ng mL$^{-1}$)+Fe-MIL-101 (12.5 µg mL$^{-1}$), CM (20 ng mL$^{-1}$)+Fe-MIL-101 (25 µg mL$^{-1}$) were added, respectively; and in the control group, DMEM was added. After treating for 24 h, the cell proteins were extracted.

Method for extracting a protein sample: Cells were washed with cold PBS and resuspended in lysis buffer (20 mM Tris-HCl, 150 mM NaCl, 1% Triton X-100, SDS, 10% β-mercaptoethanol, 1 mM PMSF, EDTA and leupeptin) for 1 h on ice. The lysates were centrifuged at 4° C. for 15 min (14,000 g).

Western blot (SDS-PAGEA electrophoresis): The extracted protein samples were separated by SDS-PAGE gel electrophoresis (concentration gel 4%, separation gel 12%), at the electrophoresis condition of U=150 V, I=50 mA; and then a wet transfer was performed, and at the electrophoresis condition of U=100 V, I=50 mA. The proteins were transferred onto PVDF membranes. After blocking the non-specific binding sites of the membranes with 5% non-fat milk in PBS-Tween, primary antibodies, MMP-2 (1:200), MMP-9 (1:200), GAPDH (1:3000), and β-actin (1:500) were added, respectively, and incubated at 4° C. overnight. On the following day, the washing was performed with PBST for three times. 1:1000-diluted HRP-conjugated secondary antibody was added. After incubation at room temperature for 1 h, the washing was performed with PBST for three times. Development and exposure to the light were performed.

Figure 10:
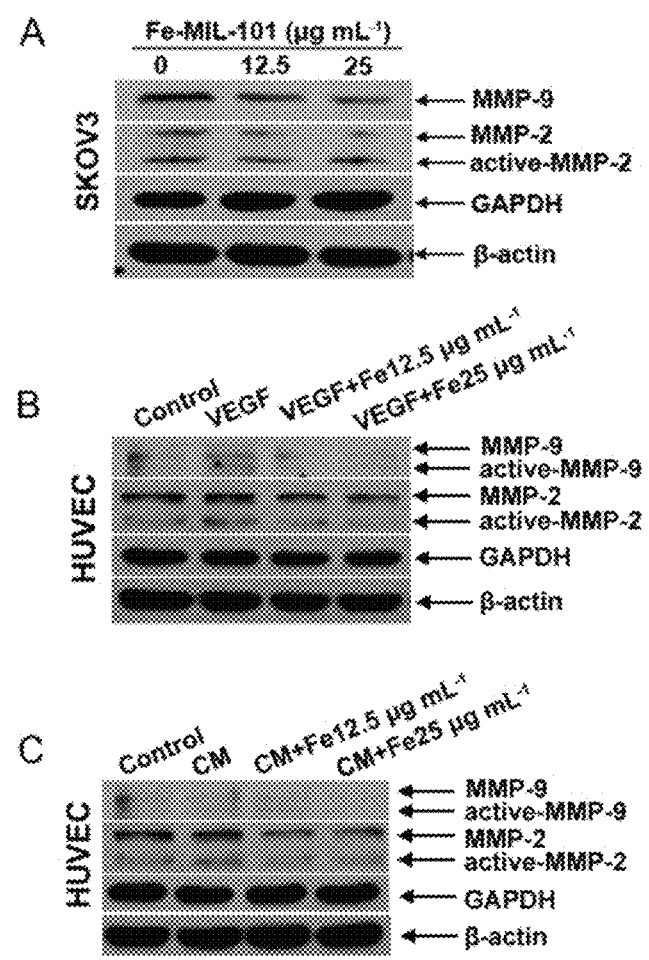

Results: FIG. 10 is the developing result, wherein FIG. 10A-C show the expression levels of MMP-2 and MMP-9 in SKOV3 cell, VEGF-stimulated HUVEC cell, and CM-stimulated HUVEC cell, respectively.

MMPs are secreted as pro-enzymes that become active when cleaved. Western blot analysis showed that the total protein expression of MMP-2 (MMP-2 and active-MMP-2) and MMP-9 markedly decreased in SKOV3 cells upon Fe-MIL-101 treatment in a dose-dependent manner (FIG. 10A). Analyses of MMPs in HUVECs showed that VEGF and CM can upregulate the expression of MMP-2, MMP-9 and their active forms (FIG. 10B, C); however, treatment with Fe-MIL-101 significantly inhibited VEGF or CM-induced upregulation of MMP expression and activities. Moreover, MMP-2/9 levels in SKOV3 cells were significantly diminished in a dose-dependent manner upon treatment with Fe-MIL-101 for 24 h.

The experimental results show that Fe-MIL-101 can inhibit the expression of matrix metalloproteinase, and can target to MMP-2 and MMP-9 enzyme.

Although the embodiments of the invention have been described in detail, a person skilled in the art will understand that according to all the disclosed teachings, various amendments and modifications may be made to the details, and the modifications all fall into the protection scope of the invention. The whole scope of the invention is defined by the attached claims or any equivalent thereof.

What is claimed is:

1. A method for inhibiting tumor angiogenesis comprising administering to a subject in need thereof an effective amount of a metal-organic framework comprising Fe and ligand, wherein the ligand is terephthalic acid; and, wherein the tumor is lung cancer or ovarian cancer, and the method does not comprise administering an additional anti-tumor agent to the subject simultaneously with the metal-organic framework.

2. The method according to claim 1, wherein the metal-organic framework comprises Fe (III).

3. The method according to claim 1, wherein the metal-organic framework is selected from a group consisting of
   1) Fe-MIL-101 which has a molecular formula of $Fe_3O(H_2O)_2F[C_6H_4(CO_2)_2)]_3$ and a crystal form of octahedron, and
   2) Fe-MIL-88B which has a molecular formula of $Fe_3O(CH_3OH)_3[C_6H_3(CO_2)_2]_3 \cdot CH_3CO_2 \cdot (CH_3OH)_{4.5}$ and a crystal form of hexangular rod.

4. The method according to claim 1, wherein the metal-organic framework is Fe-MIL-101 which has a molecular formula of $Fe_3O(H_2O)_2F[C_6H_4(CO_2)_2)]_3$ and a crystal form of octahedron.

5. The method according to claim 1, wherein the effective amount is 0.1 μg/kg/day-250 mg/kg/day.

6. The method according to claim 1, wherein the subject is a mammal.

7. A method for inhibiting tumor angiogenesis comprising administering to a subject in need thereof an effective amount of a metal-organic framework comprising Fe and ligand, wherein the ligand is terephthalic acid; and, wherein the tumor is lung cancer or ovarian cancer, wherein the metal-organic framework is administered as the only anti-tumor agent.

8. The method according to claim 7, wherein the metal-organic framework comprises Fe (III).

9. The method according to claim 7, wherein the metal-organic framework is selected from a group consisting of
   1) Fe-MIL-101 which has a molecular formula of $Fe_3O(H_2O)_2F[C_6H_4(CO_2)_2)]_3$ and a crystal form of octahedron, and
   2) Fe-MIL-88B which has a molecular formula of $Fe_3O(CH_3OH)_3[C_6H_3(CO_2)_2]_3 \cdot CH_3CO_2 \cdot (CH_3OH)_{4.5}$ and a crystal form of hexangular rod.

10. The method according to claim 7, wherein the metal-organic framework is Fe-MIL-101 which has a molecular formula of $Fe_3O(H_2O)_2F[C_6H_4(CO_2)_2)]_3$ and a crystal form of octahedron.

11. The method according to claim 7, wherein the effective amount is 0.1 μg/kg/day-250 mg/kg/day.

12. The method according to claim 7, wherein the subject is a mammal.

\* \* \* \* \*